US012802794B2

(12) United States Patent
Liu et al.

(10) Patent No.: US 12,802,794 B2
(45) Date of Patent: Nov. 17, 2026

(54) DISENTANGLED FEATURE REPRESENTATION FOR ANALYZING CONTENT AND STYLE OF RADIOLOGY REPORTS

(71) Applicant: KONINKLIJKE PHILIPS N.V., Eindhoven (NL)

(72) Inventors: Saifeng Liu, Cambridge, MA (US); Xi Wang, Belmont, MA (US); Evan Schwab, Cambridge, MA (US); Jonathan Rubin, Cambridge, MA (US); Sandeep Madhukar Dalal, Winchester, MA (US); Eran Rubens, Palo Alto, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 116 days.

(21) Appl. No.: 18/274,054

(22) PCT Filed: Jan. 28, 2022

(86) PCT No.: PCT/EP2022/052089

§ 371 (c)(1),
(2) Date: Jul. 25, 2023

(87) PCT Pub. No.: WO2022/162167

PCT Pub. Date: Aug. 4, 2022

(65) Prior Publication Data

US 2024/0428910 A1 Dec. 26, 2024

Related U.S. Application Data

(60) Provisional application No. 63/143,256, filed on Jan. 29, 2021.

(51) Int. Cl.
*G16H 15/00* (2018.01)
*G06F 40/103* (2020.01)
*G16H 30/40* (2018.01)

(52) U.S. Cl.
CPC .......... *G16H 15/00* (2018.01); *G06F 40/103* (2020.01); *G16H 30/40* (2018.01)

(58) Field of Classification Search
CPC .............................. G16H 30/40; G16H 15/00
See application file for complete search history.

(56) References Cited

U.S. PATENT DOCUMENTS

2020/0027567 A1 1/2020 Xie
2020/0311195 A1 10/2020 Mishra
2021/0082561 A1* 3/2021 Chang .................... G16H 40/63

FOREIGN PATENT DOCUMENTS

EP 3567605 A1 * 11/2019 .......... G06F 16/243
WO 2019/160557 A1 8/2019
WO 2020/214678 A1 10/2020

OTHER PUBLICATIONS

Banerjee, Imon, et al. "Intelligent word embeddings of free-text radiology reports." AMIA annual symposium proceedings. vol. 2017. 2018. (Year: 2018).*

(Continued)

*Primary Examiner* — Constantine Siozopoulos

(57) ABSTRACT

A method (100) of analyzing a medical report (34) presenting clinical content determined from one or more images (38) includes: extracting a text embedding (54) from the medical report: extracting an image embedding (52) from the one or more images; determining one or more content feature vectors from the text embedding and the image embedding; determining one or more style feature vectors from the text embedding; and at least one of: extracting one or more clinical findings contained in the medical report using the one or more content feature vectors; scoring the (Continued)

style of the medical report using the one or more style feature vectors; and/or converting the medical report to a target style using the one or more content feature vectors and one or more target style feature vectors different from the determined one or more style feature vectors.

17 Claims, 6 Drawing Sheets

(56) References Cited

OTHER PUBLICATIONS

International Search Report and Written Opinion Dated May 18, 2022 For International Application No. PCT/EP2022/052089 Filed Jan. 28, 2022.

Lao, et al: "Dual Adversarial Inference for Text-to-Image Synthesis", Aug. 14, 2019.

Kang, et al: "Distilling Content from Style for Handwritten Word Recognition", 2020 17th International Conference on Frontiers in Handwriting Recognition (ICFHR).

Vineet John: "Disentangled representation Learning for Stylistic Variation in Neural Language Models", Masters Thesis; University of Waterloo, 2018.

Bhatia, et al: "Comprehend Medical: a Named Entity Recognition and Relationship Extraction Web Service", arXiv preprint arXiv:1910.07419. Oct. 15, 2019.

Wang, et al: "TieNet: Text-image embedding network for common thorax disease classification and reporting in chest x-rays", In Proceedings of the IEEE conference on computer vision and pattern recognition 2018 (pp. 9049-9058).

Taira, et al: "Automatic structuring of radiology free-text reports", Radiographics. Jan. 2001;21(1):237-45.

Spandorfer, et al: "Deep learning to convert unstructured CT pulmonary angiography reports into structured reports", European radiology experimental. Dec. 1, 2019;3(1):37.

Lee, et al: "Diverse image-to-image translation via disentangled representations", In Proceedings of the European conference on computer vision (ECCV) 2018 (pp. 35-51).

Yang, et al: "Domain-Agnostic Learning with Anatomy-Consistent Embedding for Cross-Modality Liver Segmentation", InProceedings of the IEEE International Conference on Computer Vision Workshops 2019 (pp. 0-0).

Krause, et al: "A hierarchical approach for generating descriptive image paragraphs", InProceedings of the IEEE conference on computer vision and pattern recognition 2017 (pp. 317-325).

Jing, et al: "On the automatic generation of medical imaging reports", arXiv preprint arXiv:1711.08195. Nov. 22, 2017.

Alsentzer, et al: "Publicly available clinical BERT embeddings" arXiv preprint arXiv:1904.03323. Apr. 6, 2019.

* cited by examiner

DISENTANGLED FEATURE REPRESENTATION FOR ANALYZING CONTENT AND STYLE OF RADIOLOGY REPORTS

CROSS REFERENCE TO RELATED APPLICATIONS

This application is the U.S. National Phase application under 35 U.S.C. § 371 of International Application No. PCT/EP2022/052089 filed Jan. 28, 2022, which claims the benefit of U.S. Provisional Patent Application No. 63/143,256 filed Jan. 29, 2021. These applications are hereby incorporated by reference herein.

FIELD

The following relates generally to the medical reporting arts, radiology arts, radiology reporting arts, radiology examination reading arts, histopathology reporting arts, and related arts.

BACKGROUND

Medical reports, such as radiology reports, histopathology reports, and the like, provide written summaries of clinical findings drawn from medical images such as magnetic resonance imaging (MRI) images, computed tomography (CT) images, positron emission tomography (PET) images, or the like in the case of radiology, or microscope images in the case of histopathology. Interpretation of image features in such medical disciplines to determine actionable clinical findings (sometimes referred to as "reading" a medical examination) is a medical specialty, and the reports are typically written by domain experts, e.g. radiologists in the radiology field, or pathologists in the histopathology field. Much of the medical report is usually written in freeform text in order to enable the domain expert to capture clinical findings with a high degree of precision. Skilled radiologists and pathologists are in high demand, and often maintain heavy workloads. This can impose time constraints on performing readings of medical examinations. For example, in the clinical radiology field, some medical institutions employ a metric such as Relative Value Unit (RVU), where (as a non-limiting example) a CT reading may be assigned 4 RVU points, an MRI reading 8 RVU points, an x-ray reading 1 RVU point, and so forth. The radiologist is expected to perform readings with a certain number of total RVU points per work shift.

These time constraints, if too severe, can adversely impact accuracy of radiology readings. Hence, there is interest in developing computer aided diagnostic (CADx) tools for providing assistive automated image interpretation. For example, a CADx tool can be trained to detect tumors or lesions in a radiology image. A CADx tool can also be used for other purposes. For example, if combined with an automated tool trained to extract clinical findings from a radiology report, the CADx tool and report findings extractor can be used in tandem to assess completeness and accuracy of radiology reports.

Training of machine learning (ML) models and deep learning (DL) models for use in analyzing medical images and/or medical reports usually requires a large amount of labelled data, which can be expensive to acquire (especially for radiology data). For example, training a CADx tool to detect whether a certain finding is present in an image usually requires a large number of labeled training medical images, with each image labeled by a domain expert (e.g., skilled radiologist) as to whether the finding is present. Likewise, training a report findings extractor usually requires a large corpus of labeled medical reports which are labeled with the findings contained in those reports. There exists a large amount of unstructured and free-text radiologic reports, which can be particularly valuable for the development of artificial intelligence techniques. However, most of the radiologic reports cannot be directly used for ML or DL model development for two main reasons. First, the labels for clinical findings need to be extracted from the reports. Second, the reports are not structured, and can have various styles depending on the radiologists. The unstructured and free-text nature of the reports make it a challenging task to extract the labels accurately. The variability of the writing style of the various reports may also hinder effective analysis of the reports.

Regarding the latter issue of variable writing style, the main strategy of reducing the impact of style is structured reporting, which has been advocated to standardize the style of the report to improve reporting quality and data mining. However, structured reporting may interrupt the case viewing workflow. A structured report may also include unnecessary or redundant information, which reduce the clarity of the report. The rigid nature of structured reporting may also reduce the productivity of radiologists, and/or may limit the ability of the radiologist to convey subtleties of his or her clinical findings.

Recently-developed automatic report annotation algorithms attempt to find better ways to extract labels from the free-text radiology reports directly. These algorithms can be rule-based algorithms (e.g., CheXpert Labeller), or DL-based algorithm (e.g., Amazon Comprehend Medical and Tie-Net). Particularly, the Tie-Net algorithm utilizes both the chest x-ray images and the reports to perform a multi-modal prediction and showed promising results for report annotation and label extraction of critical findings for chest x-rays. Compared to conventional algorithms, the better performance of DL algorithms for image and report annotation is attributed to the deep and complex features extracted through convolutional neural networks (CNNs).

Using extracted features from radiologic data, there have been a few algorithms proposed for automatic generation of radiology reports, typically based on Recurrent Neural Networks (RNNs). Particularly, hierarchical Long Short-Term Memory (LSTM), with one sentence LSTM predicting the topic of a sentence and a word LSTM generating the words for that sentence, has shown great potential in generating high quality radiology reports.

The following discloses certain improvements to overcome these problems and others.

SUMMARY

In one aspect, a non-transitory computer readable medium stores instructions executable by at least one electronic processor to perform a method of analyzing a medical report presenting clinical content determined from one or more images. The method includes: extracting a text embedding from the medical report; extracting an image embedding from the one or more images; determining one or more content feature vectors from the text embedding and the image embedding, the one or more content feature vectors being indicative of clinical content presented in the medical report; determining one or more style feature vectors from the text embedding, the one or more style feature vectors being indicative of a style of the medical report; and at least one of: extracting one or more clinical findings contained in the medical report using the one or more content feature vectors; scoring the style of the medical report using the one or more style feature vectors; and/or converting the medical report to a target style using the one or more content feature vectors and one or more target style feature vectors different from the determined one or more style feature vectors.

In another aspect, an apparatus includes at least one electronic processor programmed to: extract a text embedding from a medical report; extract an image embedding from one or more images; determine one or more content feature vectors from the text embedding and the image embedding, the one or more content feature vectors being indicative of clinical content presented in the medical report; determine one or more style feature vectors from the text embedding, the one or more style feature vectors being indicative of a style of the medical report; and extract one or more clinical findings contained in the medical report using the one or more content feature vectors.

In another aspect, a method of analyzing a medical report presenting clinical content determined from one or more images includes: extracting a text embedding from the medical report; extracting an image embedding from the one or more images; determining one or more content feature vectors from the text embedding and the image embedding, the one or more content feature vectors being indicative of clinical content presented in the medical report; determining one or more style feature vectors from the text embedding, the one or more style feature vectors being indicative of a style of the medical report; and converting the medical report to a target style using the one or more content feature vectors and one or more target style feature vectors different from the determined one or more style feature vectors.

One advantage resides in providing more focused automated analyses of medical reports by separating content components and style components of the medical reports.

Another advantage resides in increasing medical report annotation accuracy, medical report effectiveness, and medical report clarity.

Another advantage resides in generating a medical report template for radiologists, pathologists, or other domain experts to use in preparing future medical reports.

Another advantage resides in performing a learning disentangled feature representation of the content and style components of the radiology report.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
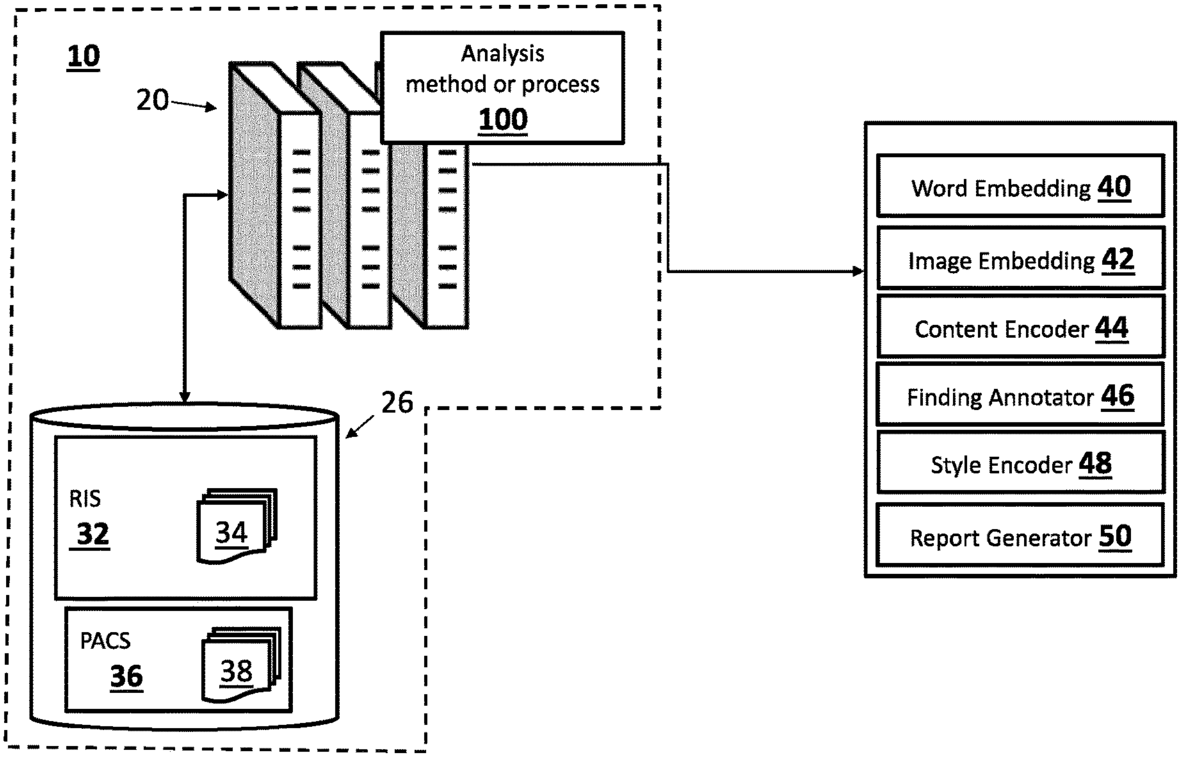
FIG. 1 diagrammatically illustrates an illustrative apparatus for analyzing radiology reports in accordance with the present disclosure.

The following relates to improvements in on automated analyses of the content of medical reports, with radiology reports being described as an illustrative example of medical reports. For example, a radiology report can be analyzed to identify clinical findings, with the results being used to assess report completeness (e.g., identify missed or erroneous findings) or to generate image labels to label training data for use in training artificial intelligence (AI) image analyzers (e.g., CADx finding detectors).

A radiologist's style in writing a report can adversely impact these tasks. That is, different radiologists may articulate the same clinical finding using different wordings, placed in different sections of the report, with different modifier words, and so forth. This style variability can adversely impact automated analyses of radiology report content. Differences in style can be reduced by using a structured radiology reporting form, but radiologists may not like being constrained to a predefined report structure.

As recognized herein, style features and content features should be independent. In particular, the content features should be the same for a given image set and should be independent of which radiologist prepared the report; whereas the style features should be the same for all reports written by a particular radiologist and should be independent of the content of those reports.

Based on the foregoing, feature disentanglement is performed to isolate a content feature vector and a style feature vector for each report. First, a report is processed to generate a text embedding. Corresponding images (that is, images that were reviewed by the radiologist, pathologist, or other domain expert and which are described or analyzed in the medical report) are processed to generate an image embedding. The text embedding can be done using a word embedding model, while the image embedding may be done using a Convolutional Neural Network (CNN), for example.

In some embodiments disclosed herein, a content encoder is trained on a training set consisting of both radiology report embeddings and the corresponding image embeddings, while a style encoder is trained on a training set consisting of only the report embeddings. Using the image embeddings in training the content encoder is expected to stabilize it. On the other hand, the style encoder is trained on only the report embeddings, because the style should be independent of the images which contain only content information. The content encoder and style encoder are typically artificial neural networks.

To ensure that the content encoder produces feature vectors that contain only content information (and not style information), in an illustrative embodiment the training includes simultaneously training the content encoder and a findings annotator by inputting the content feature vectors output by the content encoder to the findings annotator that then outputs clinical finding label vectors (e.g., binary labels in which each vector element corresponds to a finding and have a "1" or "0" value; or probability labels in which each vector element stores a probability of the corresponding finding). The training data are labeled with ground truth finding values (e.g., annotated by an expert radiologist) and the difference between the clinical finding vectors output by the findings annotator and the corresponding ground truth finding vectors is fed back as an error to the content encoder training.

To ensure that the style encoder produces feature vectors that contain only style information (and not content information), in an illustrative embodiment the training includes simultaneously training the style encoder and a report generator. The report generator is an artificial neural network that is trained to receive a content feature vector and a style feature vector and to output a text embedding. By running the report generator on content/style vector combinations that are swapped, it can be assessed as to whether the style feature vector is independent of the content.

In some embodiments disclosed herein, the trained content encoder can be applied to an input radiology report and associated images to generate a content feature vector that is then input to the co-trained findings annotator to extract the findings contained in the report. This can be used in various ways, such as for assessing report quality in terms of the actual report content.

In other embodiments disclosed herein, the trained style encoder can be applied to an input radiology report to generate a style features vector. A satisfaction predictor trained on a training set of such style feature vectors that are labeled with feedback assessments by receiving physicians can then be applied to the style features vector to predict whether receiving physicians will be likely to be satisfied with the style of the report.

In some embodiments disclosed herein, the trained content and style encoders can be used along with the report generator to transform a radiology report from one style to another style. For example, a "standard" style can be generated by running a number of reports that received positive feedback from receiving physicians through the style encoder, and taking an average of the resulting style feature vectors. Then, when a new report is received, it is processed by the content encoder to generate a corresponding content feature vector. The report generator then receives that corresponding content feature vector along with the standard style feature vector to reconstruct a report with the content of the new report but with the standard style.

While the following focuses on radiology reports, a similar approach can be used in conjunction with other types of reports that analyze image data, such as histopathology reports.

With reference to FIG. 1, an illustrative radiology report analysis apparatus 10 is implemented on an electronic processor 20, such as a server computer or illustrative multiple server computers 20 (e.g., a server cluster or farm, a cloud computing resource, or so forth), which implements a radiology report analysis method 100 presenting clinical content determined from one or more images, as disclosed herein. To perform the analysis method 100, the electronic processor 20 accesses at least one non-transitory storage medium 26 that stores at least one database 32 storing medical (for example, radiology) reports or records 34. The illustrative database(s) 32 are a Radiology Information System (RIS) which stores medical imaging-specific patient data; however, the database 32 can comprise other databases storing medical records, such as an electronic medical record (EMR) 32 (other nomenclatures may be used (e.g., electronic health record, EHR), and/or the database(s) 32 may include domain specific patient records databases such as a Picture Archiving and Communication System (PACS) database and/or a, a cardiovascular information system (CIS or CVIS) which stores patient data collected and maintained by the patient's cardiologist and/or a cardiology department, and/or so forth. In addition, the apparatus 10 includes a PACS database 36 storing images 38. As shown in FIG. 1, one or more modules can be implemented in the electronic processor 20, each of which will be described in more detail below.

The at least one electronic processor 20 is configured as described above to perform the analysis method or process 100 presenting clinical content determined from one or more images 38. The non-transitory storage medium 26 stores instructions which are readable and executable by the at least one electronic processor 20 to perform disclosed operations including performing the method or process 100. In some examples, the method 100 may be performed at least in part by cloud processing.

Figure 2:
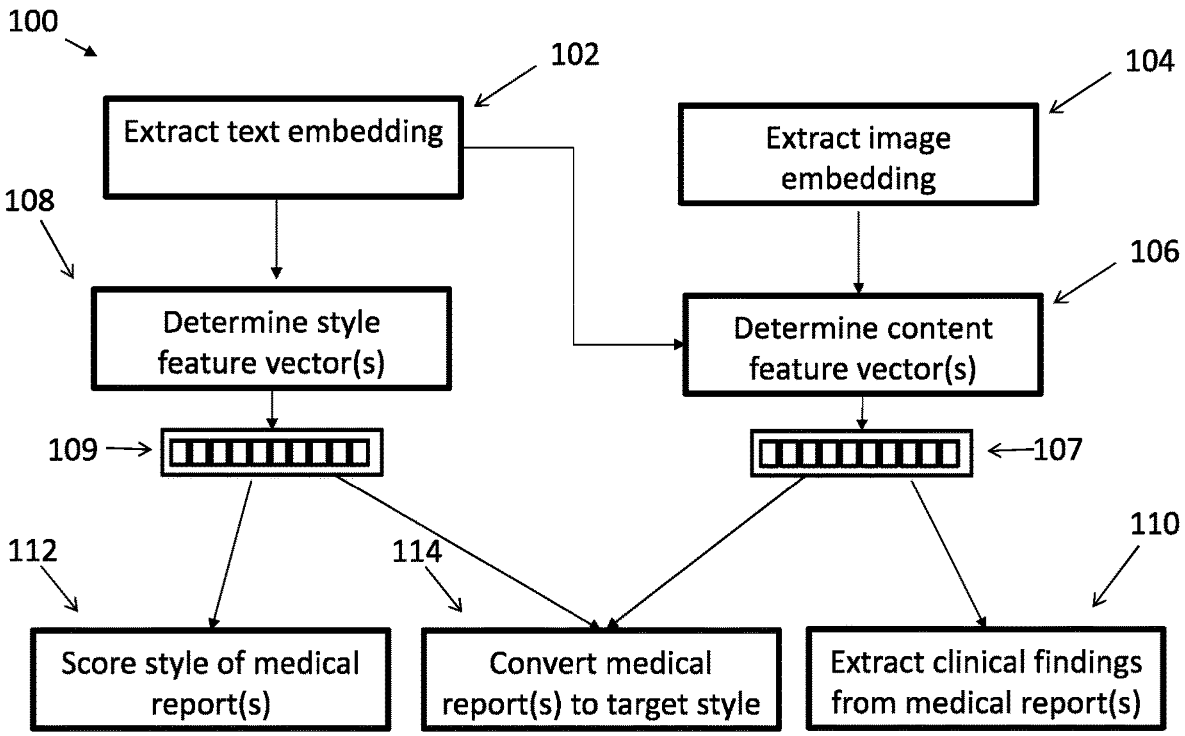
FIG. 2 shows example flow chart operations performed by the apparatus of FIG. 1.

With reference to FIG. 2, and with continuing reference to FIG. 1, an illustrative embodiment of the method 100 is diagrammatically shown as a flowchart. At an operation 102, a text embedding is extracted from a medical (i.e., radiology) report 34. This can be performed by a word embedding algorithm 40 implemented in the at least one electronic processor 20. At an operation 104, an image embedding is extracted from one or more images 38. This can be performed by an image embedding artificial neural network (NN) 42 implemented in the at least one electronic processor 20. (Note that as used herein, the term "neural network" or NN refers to an artificial neural network). The operations 102 and 104 can be performed in either order, or performed concurrently.

At an operation 106, one or more content feature vectors 107 are determined from the text embedding and the image embedding. The one or more content feature vectors 107 are indicative of clinical content presented in the medical report 34. At an operation 108, one or more style feature vectors 109 are determined from the text embedding only, and not using the image embedding. The one or more style feature vectors 109 are indicative of a style of the medical report 34. The one or more content feature vectors 107 are not indicative of the style of the medical report 34, and the one or more style feature vectors 109 are not indicative of the clinical content presented in the medical report. The operations 106 and 108 can be performed in either order, or performed concurrently. It is also noted that the term "one or more feature vectors" as used herein is intended to encompass any data structure that stores information elements, e.g. the one or more feature vectors may be a single vector, multiple vectors, a concatenation of vectors, an array having rows and columns whose elements represent elements of a single vector or of multiple vectors, and/or so forth. Such a data structure may optionally be encrypted during storage, e.g., to ensure security of patient medical information, and optionally may be encrypted during use (e.g., if homomorphic encryption is used).

In some embodiments, the content feature vector(s) and/or the style feature vector(s) can be used in training operations. In one example embodiment, a content encoder 44 and a clinical findings annotator 46 can be implemented in the at least one electronic processor 20 (see FIG. 1). The content encoder 44, which can be a NN, is used in determining the one or more content feature vectors. The clinical findings annotator 46 is configured to receive the content feature vector(s) 107 from the content encoder 44. To facilitate ensuring that the content feature vector 107 contains only content information (and not style information), in the illustrative embodiment the content encoder 44 and the clinical findings annotator 46 are co-trained using as training data the training text embeddings of training medical reports 34 presenting clinical content determined from corresponding training images 38, as well as the image embeddings of those corresponding images 38, in which the training medical reports are labeled as to clinical findings contained in the training medical reports.

To co-train the content encoder 44 and the findings annotator 46, the content feature vector(s) and the corresponding image feature vectors are input to the content encoder 44, and the content vector 107 output by the content encoder 44 is then input to the findings annotator 46. The parameters (e.g., NN weights and activation functions) of the content encoder 44 and the findings annotator 46 are optimized using backpropagation and/or other NN training techniques to design the content encoder 44 and the findings annotator 46 to output findings that optimally match the finding labels of the training data which serve as ground truth values.

In the illustrative embodiment, a style encoder 48 and a report generator 50 can be implemented in the at least one electronic processor 20. The style encoder 48, which can be a NN, is used in determining the one or more style feature vectors 109, and the report generator 50 is configured to generate the medical reports 34. The style encoder 48 and the report generator 50 are co-trained using training text embeddings of training medical reports 34 presenting clinical content determined from corresponding training images 38.

To co-train the style encoder 48 and the report generator 50, the text embedding (but not the image embedding) is input to the style encoder 48 to generate the style feature vector(s) 109. Content feature vector(s) 107 generated by the content encoder 44 for other reports are used with the style feature vector(s) 109 as inputs to the report generator 50. Text embeddings are output for these various content/style combinations by the report generator. A determination is made as to whether the one or more style features vectors are independent of the one or more content features vectors.

With reference back to FIG. 2, the content feature vector(s) and the style feature vector(s) determined by the trained components 106, 108 for a given input radiology report can be used in a variety of manners. In one example embodiment, at an operation 110, one or more clinical findings contained in the medical report 34 are extracted from the content feature vector(s) 107. Advantageously, since the content feature vector(s) 107 contain only content information that has been disentangled from the style information by the trained content encoder 44, the clinical findings extraction 110 is expected to be more accurate than such an extraction applied directly to the text embedding which contains entangled content and style information. In another example embodiment, at an operation 112, a style of the medical report 34 can be scored using the style feature vector(s) 109. Advantageously, since the style feature vector(s) 109 contain only style information that has been disentangled from the content information by the trained style encoder 48, the style analysis is expected to be more accurate than such an analysis applied directly to the text embedding which contains entangled content and style information. In yet another example embodiment, at an operation 114, the medical report 34 is converted 114 to a target style or format using both the content feature vector(s) 107 and the style feature vector(s) 109. Specifically, by inputting to the report generator 50 a content feature vector 107 from a radiology report to be converted and a style feature vector 109 representing the target style, the resulting reconstructed radiology report contains the desired content but presented in the target style.

EXAMPLE

Figure 3:
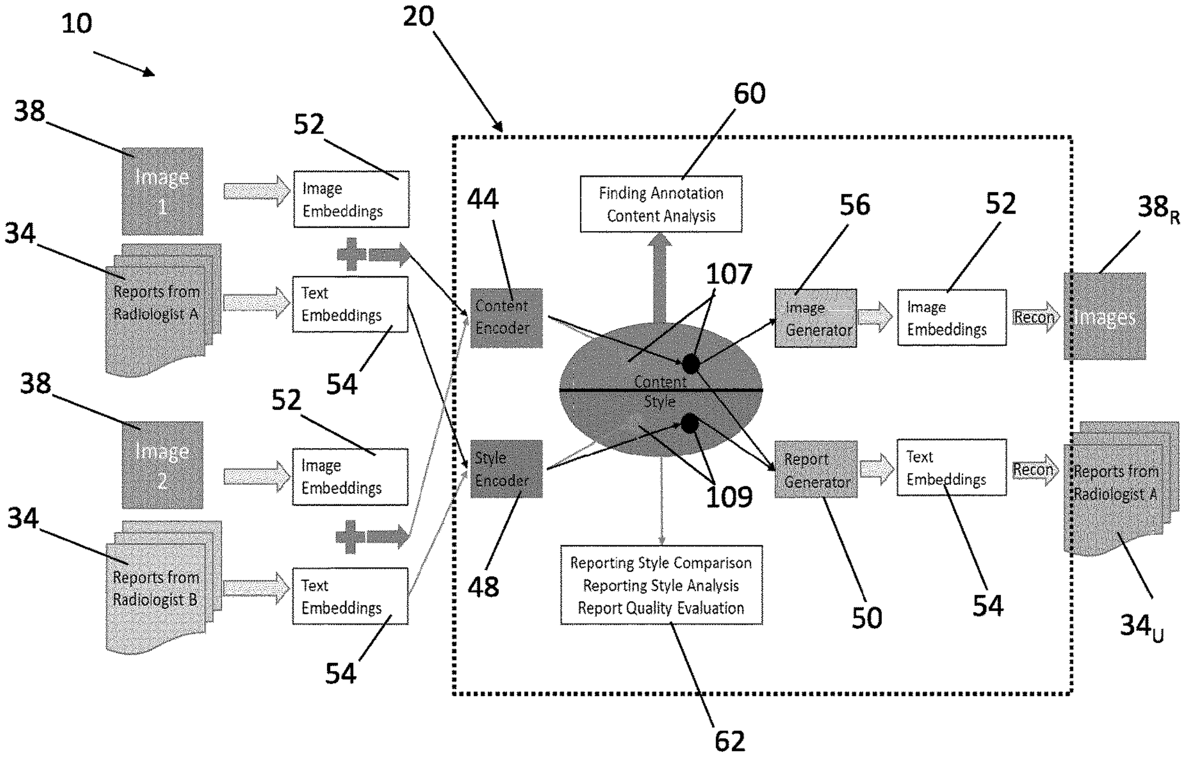
FIG. 3 shows another embodiment of the apparatus of FIG. 1.

FIG. 3 shows another example of the apparatus 10. As shown in FIG. 3, the reports 34 composed by different radiologists are considered as different domains. Each report 34 can be represented by a content feature vector and a style feature vector. Furthermore, a single style feature vector can be extracted from the reports 34 written by the same radiologist. Both the reports 34 and the associated images 38 are used to improve the quality and accuracy of extracted content features. The style feature vector(s) are extracted from reports 34 only. The images 38 and reports 34 from radiologist A and B do not need to be paired data (i.e., images 1 and 2 do not need to be the same case).

The apparatus 10 utilizes both data from the images 38 and the reports 34 as input. It is not required to have the same case reviewed by different radiologist, but it is assumed that the images 38 are of the same kind (e.g., modality and/or anatomy imaged, such as chest x-rays). Labels can be required, which are suitably M×1 binary vectors, to indicate whether a finding/concept is present in the report 34. "M" is the number of finding/concept categories. For image data, image embeddings 52 can be extracted using an imaging embedding Convolutional Neural Network (CNN) 42. For report data, text embeddings 54 can be obtained using the pre-trained word embedding models 40.

The image and text embeddings 52, 54 are input to content encoder 44 to generate the content feature vectors 107, while the text embeddings 54 alone are input to the style encoder 48 to generate the style feature vectors 109. The use of image and report data jointly for content feature extracting improves the reliability of the content and stabilizes the model training. These encoders 44, 48 are suitably NNs which map the embeddings to two vectors/features-a content feature and a style feature. The content encoder 44 is, in one illustrative example, composed of a CNN which extracts features from image data (here, the image embeddings 52), and a Transformer-based neural network which extracts features from text data (here, the text embeddings 54). The style encoder 48, in one illustrative embodiment, contains a Transformer-based neural network only.

The content feature vectors 107 and style feature vectors 109 can be input to the report generator 50 (and optionally to an image generator 56) to recover the image and text embeddings 52, 54. Similar to the encoders 44, 48, the image generator 56 is a CNN and the input thereto is the content feature, while the report generator 50 is a Transformer-based neural network and the input thereto is the content features and style features. Next, the image embeddings 52 can be input to another CNN to reconstruct the images 38R with the original dimensions, and the text embeddings 54 can be fed into a look-up-table or another Transformer-based neural network to generate updated reports 34*u*. (In an alternative embodiment, the image generator 56 is omitted, and the original images 38 are retained rather than reconstructed. However, reconstructing the images using the image generator 56 can provide a check on performance of the image embedding process.)

FIG. 3 also shows a Finding Annotation/Content Analysis 60 and a Reporting Style Comparison/Reporting Style Analysis/Report Quality Evaluation 62. Report annotation and categorization can be performed using the content feature vectors 107, since these vectors are independent of reporting style. This will significantly improve the accuracy and robustness of the analysis of report content in the reports 34. The content encoder 44 in the trained model can be used as a feature extractor for the development of models for analyzing report content. To do so, a report annotation or label extraction model can be developed, by the content encoder 44 when labels for the presence of findings are available. Second, one or more report content categorization models can be developed by the content encoder 44, to classify the report content into qualitative, comparative or recommendations related categories. This can be valuable for ensuring the completeness of the report 34. To train these models, the content feature vectors 107 can be used by the Finding Annotation/Content Analysis 60 to predict the presence of a finding or a concept, (e.g., pneumothorax). A cross-entropy loss can be used to evaluate the prediction against the ground-truth labels of the findings or concepts according to Equation 1:

$$L_{finding} = -\frac{1}{N}\sum_{i}^{N}\sum_{c=1}^{M} y_{i,c}\log(p_{i,c}) \tag{1}$$

where M represents the number of finding types, $y_{i,c}$ is an indicator variable which equals 1 if sample i belongs to class c. $p_{i,c}$ is the predicted probability of sample i belongs to class c, and N is the total number of samples in the training set.

Figure 4:
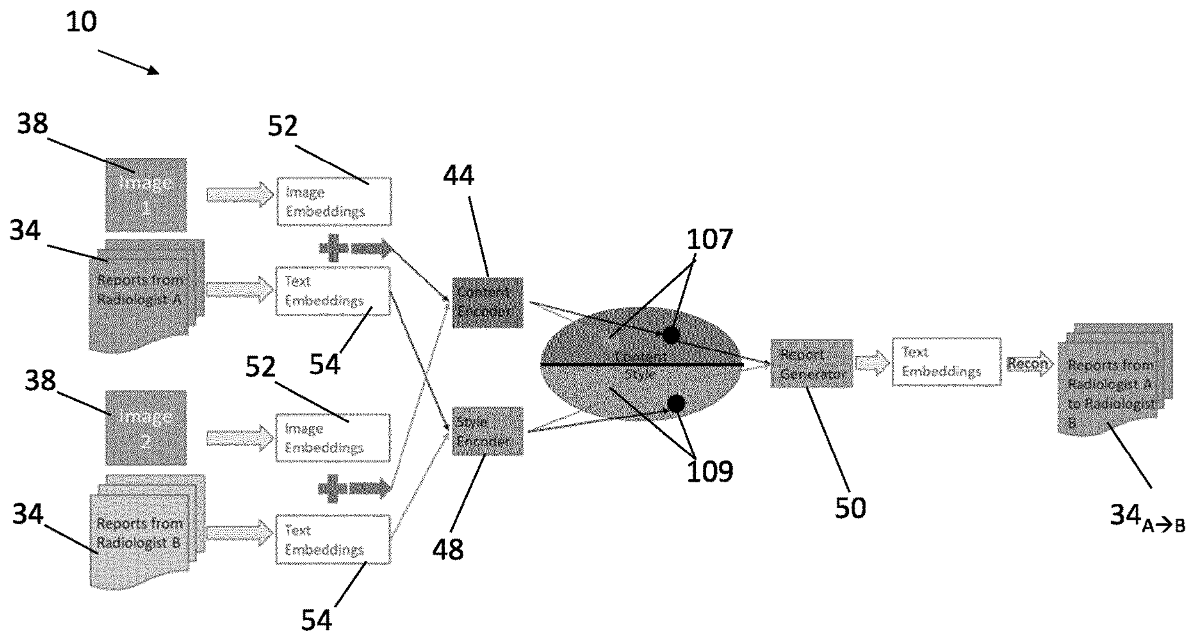
FIG. 4 shows an application of the apparatus of FIG. 1 for transferring a radiology report style of a second radiologist to a radiology report prepared by a first radiologist.

With continuing reference to FIG. 3 and with further reference to FIG. 4, once the content and style feature vectors 107, 109 of a given report 34 from a first radiologist A are extracted, these feature vectors can be swapped with a corresponding feature vector one extracted from another report by a second (different) radiologist B. The original feature vector and the swapped feature vector can be combined and input to the report generator 50 to perform report style transfer, while the content of the report 34 is preserved, so as to output a style-transformed report $\mathbf{34}_{A\rightarrow B}$ which has the content of the report by radiologist A but with the style of radiologist B.

Figure 5:
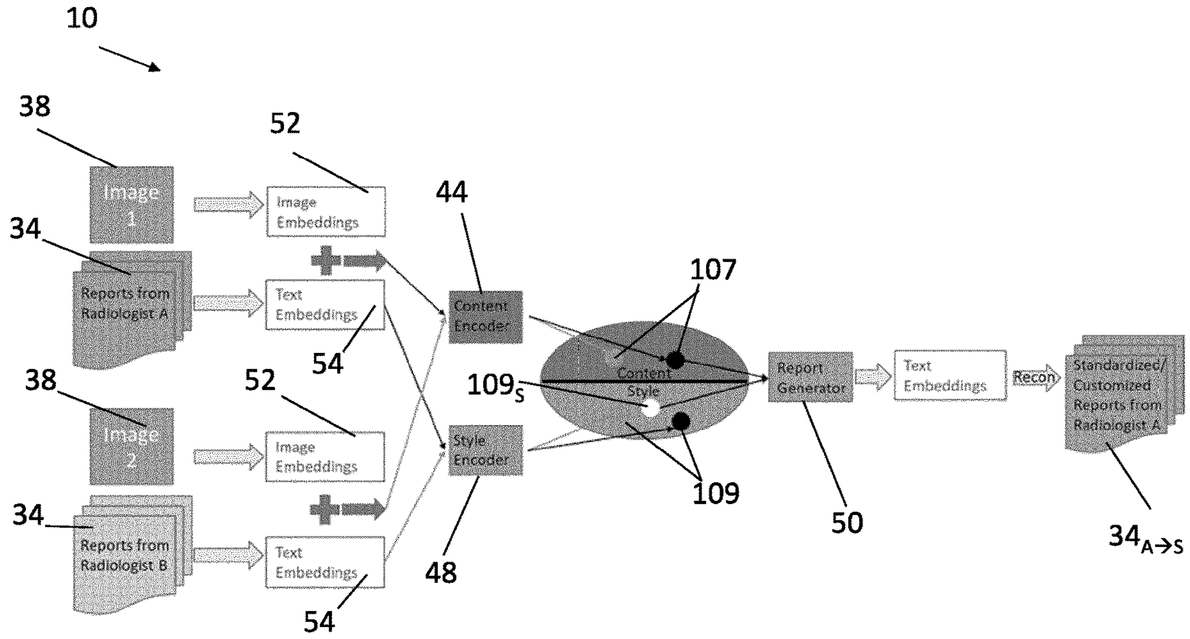
FIG. 5 shows an application of the apparatus of FIG. 1 for transferring a standard report style to a radiology report prepared by a radiologist.

With continuing reference to FIG. 3 and with further reference to FIG. 5, instead of using any style feature vector of any specific report, a standard style vector 109*s* can be created from a group of manually selected reports 34, which have high quality. Using this standard style vector 109*s*, the style of any report 34 (e.g., by radiologist A in FIG. 5) can be transferred to a standardized style (i.e., the operation 114), so as to output a style-transformed report $\mathbf{34}_{A\rightarrow S}$ which has the content of the report by radiologist A but with the standard style represented by the standard style vector 109*s*. Similarly, the style from a user-preferred report can be used as the standard style vector 109*s* to guide the style transfer to generate a report 34 with customized style.

These are merely illustrative applications. In another example application (not shown), the style features of two reports 34 can also be used to compute a quantitative distance to reflect the similarity of two reports. In another example application (not shown), by comparing with a standard report style, a report outlier detection can be achieved. This can also be used for training radiology residents on report writing.

To train the style encoder 48 and the report generator 50, an adversarial loss algorithm can be used. Specifically, for a given pair of training samples, with one report 34 from, for example, radiologist A and another report 34 from, for example, radiologist B, their extracted style features can be swapped, and the reconstructed text embeddings can be indistinguishable from the original reports with the same style (but different content) according to Equation 2:

$$L^a = E[\log D_2(r_2) + \log(1 - D_2(G(c_1, s_2)))] + E[\log D_1(r_1) + \log(1 - D_1(G(c_2, s_1)))] \tag{2}$$

where $D_i$ (i=1 or 2) is a discriminator for report ($r_i$) written by radiologist i, $c_i$ and $s_i$ are the content and style features extracted from the report.

To train the report generator 50, a combination of reconstruction loss and adversarial loss can be used according to Equation 3:

$$L_{report} = R(E_{report}, E'_{report}) + \lambda_a L^a \tag{3}$$

where R is a loss function which evaluates the distance between the original ($E_{report}$) and reconstructed $$(E'_{report})$$

text embeddings. Examples of R include L1 norm and L2 norm. La is the adversarial loss shown in Equation 2, and $\lambda_a$ is a weighting constant. The image generator network can be trained using a similar loss function shown in Equation 3.

Figure 6:
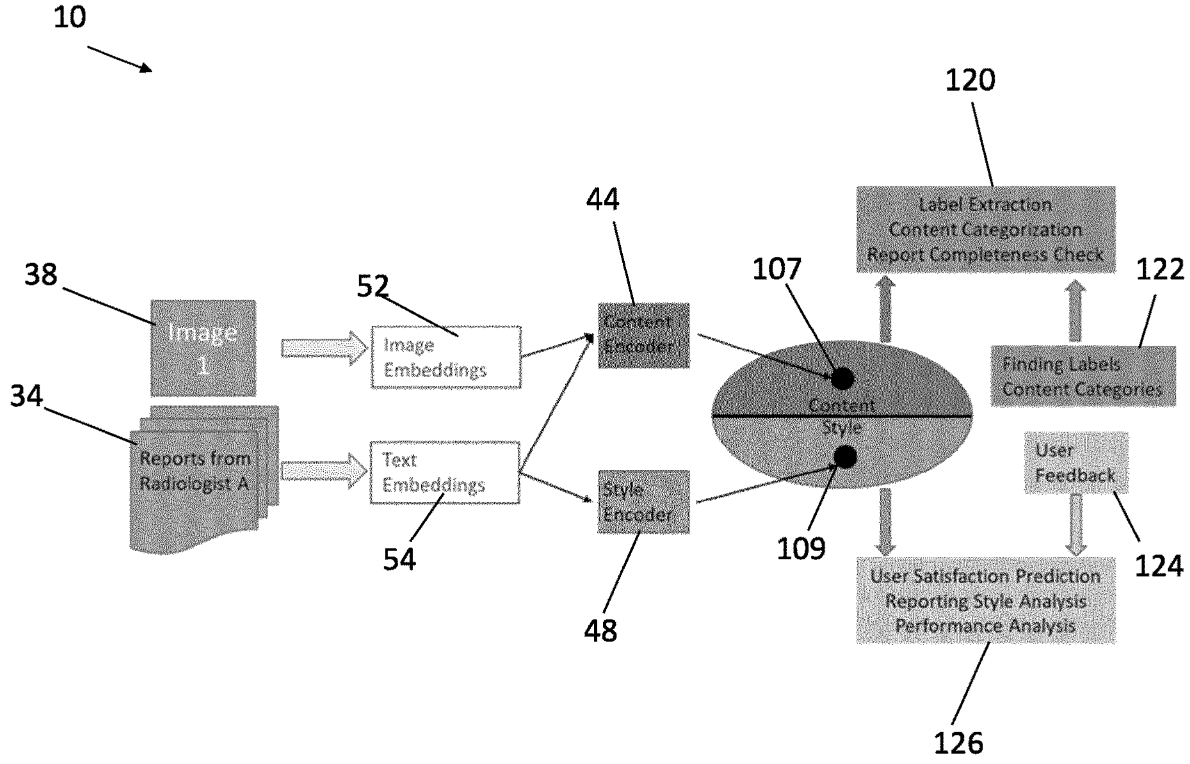
FIG. 6 shows illustrative radiology report analytics suitably performed using the apparatus of FIG. 1.

With reference to FIG. 6, the style feature vectors extracted from the reports 34 can be used to provide analytics regarding the effectiveness of communication between radiologists and referring clinicians or patients, to improve end-user satisfaction. For this purpose, feedback is collected from end-users. As shown in FIG. 6, a content-related analytic 120 checks report completeness based on the findings extracted from the content feature vector(s) 107 compared against some ground truth finding information 122 (for example, manually generated by a high-level radiologist performing the same reading). Correlation between reporting style and user feedback 124 can be studied by a style analytic 126, and a machine learning model implemented by the at least one electronic processor 20 can be developed to predict end-user satisfaction.

The apparatus 10 can be used for improving radiology data annotation in many applications, including generating high-quality labels which can be used for developing machine learning and deep learning techniques; generating radiology reports with standardized or customized style, while preserving the content; transferring the style of a report to the style of another report; measuring the similarity of two radiology reports based on their styles; training radiology residents on report writing by evaluating content completeness and reporting style; detecting radiology report outliers in terms of style; development of report analytics models such as report content categorization, content completeness check correlation between user satisfaction and reporting style; among others.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A computer-implemented method of generating annotated images of clinical findings, the method comprising:

obtaining a medical report presenting clinical content determined from one or more images, the medical report comprising a style;

extracting a text embedding from the medical report;

extracting, using a trained neural network, an image embedding from the one or more images;

determining one or more content feature vectors from the text embedding and the image embedding, the one or more content feature vectors being indicative of clinical content presented in the medical report, wherein the one or more determined content feature vectors are not indicative of the style of the medical report;

determining, using a style encoder, one or more style feature vectors from only the text embedding, the one or more style feature vectors being indicative of a style of the medical report, wherein the one or more determined style feature vectors are not indicative of the clinical content presented in the medical report;

converting the medical report to a target style using the determined one or more content feature vectors and the determined one or more target style feature vectors;

determining one or more clinical findings contained in the medical report based on the determined one or more content feature vectors; and constructing a plurality of annotated medical images with one or more finding labels corresponding to the determined one or more clinical findings based on the target style, wherein the plurality of annotated medical images are configured to train a machine learning model to detect a clinical feature in a medical image.

2. The method of claim 1, further comprising:

co-training a content encoder used in determining the one or more content feature vectors and a clinical findings annotator that receives the one or more content feature vectors from the content encoder using training text embeddings of training medical reports presenting clinical content determined from corresponding training images in which the training medical reports are labeled as to clinical findings contained in the training medical reports.

3. The method of claim 1, further comprising:

co-training the style encoder used in determining the one or more style feature vectors and a report generator using training text embeddings of training medical reports presenting clinical content determined from corresponding training images.

4. The method of claim 3, wherein the content encoder comprises a neural network (NN) and the style encoder comprises a NN.

5. The method of claim 2, further comprising:

training the content encoder and the clinical findings annotator with the one or more content features vectors;

outputting clinical finding label vectors from the training;

labelling the one or more content features vectors with ground truth finding values to generate ground truth finding vectors; and inputting a difference between the clinical finding label vectors and the ground truth finding vectors to the content encoder.

6. The method of claim 3, further comprising:

training the report generator and the style encoder with the one or more content features vectors and the one or more style features vectors;

outputting a text embedding from the training; and determining whether the one or more style features vectors are independent of the one or more content features vectors.

7. The method of claim 1, wherein the style of the medical report includes one or more wordings whereby the one or more clinical findings are articulated.

8. The method of claim 1, wherein the style of the medical report includes one or more placements of the one or more clinical findings in sections of the medical report.

9. The method of claim 1, wherein the style of the medical report includes the use of one or more modifier words.

10. The method of claim 1, wherein the report is a radiology report.

11. The method of claim 1, further comprising:

scoring the style of the medical report using the one or more style feature vectors; and converting the medical report to the target style using the determined one or more content feature vectors, the determined one or more target style feature vectors, and the scored style.

12. An apparatus for generating annotated images of clinical findings, comprising:

at least one electronic processor programmed to:

obtain a medical report presenting clinical content determined from one or more images, the medical report comprising a style;

extract a text embedding from a medical report;

extract, using a trained neural network, an image embedding from one or more images;

determine one or more content feature vectors from the text embedding and the image embedding, the one or more content feature vectors being indicative of clinical content presented in the medical report, wherein the one or more determined content feature vectors are not indicative of the style of the medical report;

determine, using a style encoder, one or more style feature vectors from only the extracted text embedding, the one or more style feature vectors being indicative of a style of the medical report, wherein the one or more determined style feature vectors are not indicative of the clinical content presented in the medical report;

convert the medical report to a target style using the determined one or more content feature vectors and the determined one or more target style feature vectors;

determine one or more clinical findings contained in the medical report based on the one or more content feature vectors; and construct a plurality of annotated medical images with one or more finding labels corresponding to the determined one or more clinical findings based on the target style, wherein the plurality of annotated medical images are configured to train a machine learning model to detect a clinical feature in a medical image.

13. The apparatus of claim 12, wherein the at least one electronic processor is further programmed to:

co-train a content encoder used in determining the one or more content feature vectors and a clinical findings annotator that receives the one or more content feature vectors from the content encoder using training text embeddings of training medical reports presenting clinical content determined from corresponding training images in which the training medical reports are labeled as to clinical findings contained in the training medical reports.

14. The apparatus of claim 12, wherein the at least one electronic processor is further programmed to:

co-train a style encoder used in determining the one or more style feature vectors and a report generator using training text embeddings of training medical reports presenting clinical content determined from corresponding training images.

15. The apparatus of claim 12, wherein the at least one electronic processor is further programmed to at least one of:

score the style of the medical report using the one or more style feature vectors; and convert the medical report to the target style using the determined one or more content feature vectors, the determined one or more target style feature vectors, and the scored style.

16. A non-transitory computer-readable storage medium having stored a computer program comprising instructions, which, when executed by a processor, cause the processor to:

obtain a medical report presenting clinical content determined from one or more images, the medical report comprising a style;

extract a text embedding from the medical report;

extract, using a trained neural network, an image embedding from the one or more images;

determine one or more content feature vectors from the text embedding and the image embedding, the one or more content feature vectors being indicative of clinical content presented in the medical report, wherein the one or more determined content feature vectors are not indicative of the style of the medical report;

determine, using a style encoder, one or more style feature vectors from only the text embedding, the one or more style feature vectors being indicative of a style of the medical report, wherein the one or more determined style feature vectors are not indicative of the clinical content presented in the medical report;

convert the medical report to a target style using the determined one or more content feature vectors and the determined one or more target style feature vectors;

determine one or more clinical findings contained in the medical report based on the one or more content feature vectors; and construct a plurality of annotated medical images with one or more finding labels corresponding to the determined one or more clinical finding based on the target style, wherein the plurality of annotated medical images are configured to train a machine learning model to detect a clinical feature in a medical image.

17. The non-transitory computer-readable storage medium of claim 16, wherein the instructions, when executed by the processor, further cause the processor to:

score the style of the medical report using the one or more style feature vectors; and convert the medical report to the target style using the determined one or more content feature vectors, the determined one or more target style feature vectors, and the scored style.

* * * * *